United States Patent
Swoyer et al.

(10) Patent No.: US 8,874,235 B1
(45) Date of Patent: Oct. 28, 2014

(54) SELF FIXING SPINAL CORD STIMULATION PADDLE LEAD

(75) Inventors: John M. Swoyer, Andover, MN (US); Scott Kokones, Boston, MA (US)

(73) Assignee: Greatbatch Ltd., Clarence, NY (US)

( * ) Notice: Subject to any disclaimer, the term of this patent is extended or adjusted under 35 U.S.C. 154(b) by 942 days.

(21) Appl. No.: 12/637,131

(22) Filed: Dec. 14, 2009

Related U.S. Application Data

(60) Provisional application No. 61/121,966, filed on Dec. 12, 2008.

(51) Int. Cl.
*A61N 1/05* (2006.01)
*A61B 5/042* (2006.01)

(52) U.S. Cl.
CPC ............ *A61N 1/0551* (2013.01); *A61N 1/0553* (2013.01); *A61B 5/042* (2013.01)
USPC ............................ 607/117; 607/116; 600/373

(58) Field of Classification Search
CPC ..... A61N 1/0551; A61N 1/0553; A61B 5/042
USPC ............................ 607/116–117, 148; 600/373
See application file for complete search history.

(56) References Cited

U.S. PATENT DOCUMENTS

| | | | |
|---|---|---|---|
| 6,999,820 B2 | 2/2006 | Jordan | |
| 7,006,875 B1 | 2/2006 | Kuzma et al. | |
| 7,613,524 B2 | 11/2009 | Jordan | |
| 7,620,454 B2 | 11/2009 | Dinsmoor et al. | |
| 2002/0111661 A1 | 8/2002 | Cross et al. | |
| 2004/0039417 A1 | 2/2004 | Soykan et al. | |
| 2004/0049240 A1 | 3/2004 | Gerber et al. | |
| 2004/0106959 A1 | 6/2004 | Schmidt et al. | |
| 2004/0236381 A1 | 11/2004 | Dinsmoor et al. | |
| 2004/0236382 A1 | 11/2004 | Dinsmoor et al. | |
| 2004/0243208 A1 | 12/2004 | Jordan | |
| 2004/0243241 A1 | 12/2004 | Istephanous et al. | |
| 2005/0033393 A1 | 2/2005 | Daglow | |
| 2005/0154435 A1 | 7/2005 | Stern et al. | |
| 2006/0052856 A1 | 3/2006 | Kim et al. | |
| 2006/0206164 A1 | 9/2006 | Gavronsky | |
| 2007/0055332 A1* | 3/2007 | Swoyer ......................... | 607/117 |
| 2007/0173914 A1* | 7/2007 | Kollatschny .................. | 607/116 |
| 2008/0132961 A1 | 6/2008 | Jaax et al. | |
| 2008/0161884 A1* | 7/2008 | Chandler et al. ............... | 607/50 |
| 2008/0234791 A1* | 9/2008 | Arle et al. ..................... | 607/117 |
| 2008/0275523 A1 | 11/2008 | Tvaska | |
| 2009/0112282 A1 | 4/2009 | Kast et al. | |

FOREIGN PATENT DOCUMENTS

| | | |
|---|---|---|
| EP | 0818123 B1 | 1/2003 |
| EP | 1171198 B1 | 7/2005 |
| EP | 0950426 A1 | 2/2009 |
| EP | 2108398 A1 | 10/2009 |
| WO | WO9704702 | 2/1997 |

(Continued)

*Primary Examiner* — Tammie K Heller
(74) *Attorney, Agent, or Firm* — Michael F. Scalise

(57) ABSTRACT

An improved electrical neurological stimulation paddle lead is described. The paddle lead comprises two flexible concave paddle bodies that are joined together at their opposing convex surfaces. The first paddle body contains a series of electrodes that are embedded on the concave surface that expand to fit the contours of the dura mater. The second paddle body consists of a concave surface that is pressed against the bone of the spinal column to act as a fixation mechanism to keep the paddle assembly in place.

20 Claims, 3 Drawing Sheets

(56) References Cited

FOREIGN PATENT DOCUMENTS

| WO | WO9840120 | 9/1998 |
| WO | WO02072194 | 9/2002 |
| WO | WO2006115772 | 11/2006 |
| WO | WO2006119468 | 11/2006 |
| WO | WO2008051926 | 5/2008 |

* cited by examiner

SELF FIXING SPINAL CORD STIMULATION PADDLE LEAD

CROSS-REFERENCE TO RELATED APPLICATION

The present application claims priority from U.S. Provisional Application Ser. No. 61/121,966 filed Dec. 12, 2008.

BACKGROUND OF THE INVENTION

1. Field of the Invention

The present invention is related generally to implantable medical electrical leads. More specifically, the present invention is related to implantable neurological leads.

2. Prior Art

Neurostimulation is the application of electrical energy to neurological tissue to block the sensation of pain. A medical device, specifically an implanted neurostimulator generates an electrical pulse which is emitted from a connected lead that is implanted in the body.

Despite the many advances in neurostimulation, many problems still exist with the technology that have yet to be optimized. One of which is lead migration, the second being energy efficiency.

An ideal neurostimulation lead is designed to remain in position and emit electrical energy to a specific targeted nerve or array of nerves in an energy efficient manner. However the geometric constraints of the human anatomy sometimes make it difficult to stimulate the targeted neurological tissue in an energy efficient manner. The confined spaces of the spinal column add an increased element of complexity to neurological tissue stimulation. In addition, the delicate nature of the neurological tissue make lead fixation challenging.

One such neurostimulator lead is the percutaneous lead. This lead has a long lumen with a small cylindrical diameter. Discrete metal electrode bands are wrapped circumferentially around the proximal and distal regions of the cylindrical lumen of the lead.

The small cylindrical diameter and long slender length of the lead make it advantageous for implantation into a patient with minimal tissue trauma. Percutaneous leads are typically inserted through a small opening in the patient and advanced into position from outside a patient's body. However, despite their advantages of implantation, percutaneous leads are often ineffective in targeting specific neurological tissue in an energy efficient manner.

Using a neurostimulator implantable medical device, electrical signals are programmed to be emitted from selected electrode bands around the lead. Once activated, the percutaneous lead radially broadcast electrical energy all around the circumference of the electrode band. The lead indiscriminately emits electrical energy 360 degrees completely around the lead body in the hope of hitting the desired location of the neurological tissue.

This approach does not efficiently utilize the electrical energy of the medical device. A significant amount of electrical energy is transmitted in unintended directions away from the targeted neurological tissue. As a result of the indiscriminately broadcasted energy, a power burden is placed on the implanted medical device. This causes the device's power supply to be drained at a faster rate, thus requiring the device's power supply to be frequently replenished either through recharging or replacement. Percutanous leads also lack a fixation mechanism which makes them prone to movement within the body.

An alternative neurostimulation lead that has been designed to improve energy efficiency is referred to by those skilled in the art as a paddle lead. As its name implies, the paddle lead has a flat rectangular distal end resembling a paddle. The traditional paddle body is rectangular in shape with flat planar top and bottom sides. Electrical energy is emitted from an array of electrode pads which are typically embedded in one side of the paddle body.

Since paddle leads only have electrodes on one side, unlike that of percutaneous leads, the paddle lead can only emit electrical energy in a 180 degree semi-spherical arc from the paddle surface. Therefore, paddle leads are more energy efficient than percutaneous leads. However, a disadvantage to the traditional paddle lead is that they are typically designed with a top and bottom planar surface that do not conform to curved surfaces. This is not an ideal shape for focusing electrical energy to a specific location located around a cylindrical spinal column and spinal cord. Traditional paddle leads are an improvement in energy efficiency from percutaneous leads, however, more is desired in focusing the electrical energy to a specific area or point of neurological tissue.

Having a lead with a curved surface facing the spinal column improves the ability to focus electrical energy to specific neurological tissue and would allow for more uniform spacing between the paddle body at the distal end of the lead and the spinal column. Unfortunately, this shape alone without a fixation mechanism, would allow for the paddle body to rotate in the epidural space of the spinal column with little resistance. Paddle leads lack a fixation mechanism and therefore are susceptible to lead migration.

A curved wing paddle design is disclosed in U.S. Pat. Nos. 6,999,820 and 7,613,524, both to Jordan. As stated in both the '820 and '524 patents, "the wings on the outer edge of the lead serve to stabilize and immobilize the lead with respect to the targeted tissue and assist in focusing the electrical energy".

However the winged electrode body design by Jordan is one rigid piece that lacks a fixation mechanism. Because of its rigid wing design, the paddle is free to rotate around the spinal cord with little resistance. This kind of movement could cause the paddle electrode to move further away from the target nerve and possibly result in an increase in the amount of cerebrospinal fluid (CSF) between the electrode and target nerve. CSF is a biological fluid that flows between the spinal cord and dura mater. An increase in CSF between the electrodes and targeted neurological tissue is not desired because it decreases the electrical efficiency of the system.

What is desired is a more energy efficient lead that conforms to the spinal column and incorporates a fixation mechanism for holding the lead in place to minimize rotation, movement and migration of the lead when implanted in the body.

SUMMARY OF THE INVENTION

The present invention is a paddle lead that is designed to address the shortcomings of the prior art. The disclosed paddle lead is one that is more energy efficient, provides a fixation mechanism and improves the directional control of the electrical signal.

Specifically, the present invention is a neurostimulator lead with a double curved flexible paddle assembly design. The paddle assembly consists of two curved paddles (a right side paddle and a left side paddle) with opposing flexible concave front sides that are connected at the apex region of the curvature of the convex backsides. Both right and left side paddles are composed of a biocompatible polymer that adds flexibility and resiliency to the paddles. The right side of the assembly is designed to be placed in contact with the bone of the spinal column as the fixation mechanism whereas the opposing left side with an array of embedded electrodes is designed to compress against the dura mater, a neurological tissue membrane which surrounds the spinal cord.

Once implanted into the epidural space of the spinal column, the concave end portions of the right side compress against the bone of the spinal column, acting like a spring in pushing the opposing left side paddle forward into the dura mater, fixating the paddle assembly in place.

The concave surface of the left side expands and conforms to the contours of the curved neurological tissue, such as the dura mater of the spinal cord. The embedded electrodes in the surface of the left paddle are also compressed into the dura mater of the spinal cord, thereby providing improved directional control of the stimulation signal.

Compression of the left paddle into the neurological tissue restricts the flow of cerebrospinal fluid (CSF) which flows between the dura mater and the spinal cord on the side of the implanted paddle assembly. As will be discussed in more detail, restriction of CSF is desirable in increasing the energy efficiency of the medical device.

DETAILED DESCRIPTION OF THE PREFERRED EMBODIMENTS

Figure 1A:
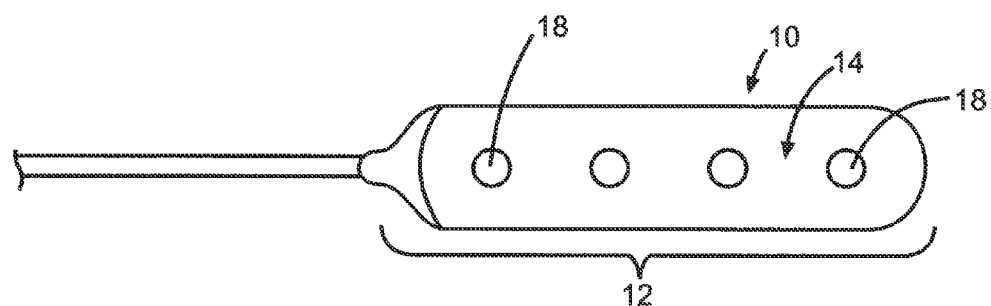
FIG. 1A is a perspective view of a prior art neurological stimulator paddle lead 10.
Figure 1B:
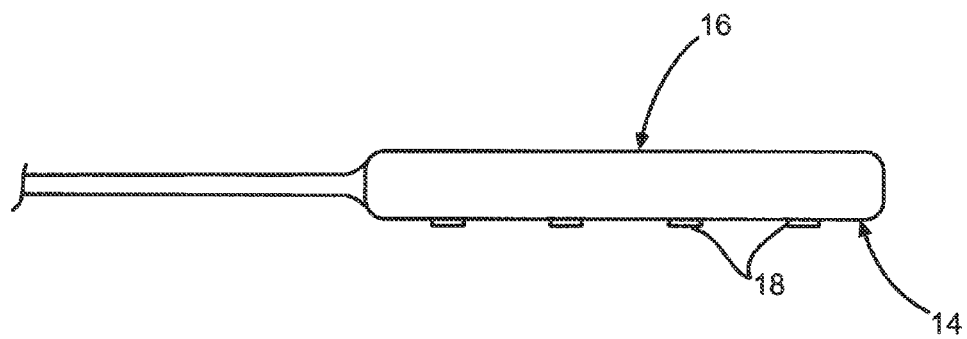
FIG. 1B is a side view of the prior art paddle lead 10 shown in FIG. 1A.

FIGS. 1A and 1B show an example of a traditional prior art paddle lead 10. The distal end of the lead 12 has an extension that resembles a paddle. The distal extension is typically a rectangular body with a planar top surface 14 and a planar bottom surface 16. Electrodes 18 are embedded within the top surface 14. As previously mentioned, this lead design is not optimized to fit properly in the curved confines of the epidural space between the spinal column and the dura mater and, as such, does not provide an efficient means to direct electrical energy to stimulate the spinal cord. In addition, this lead design lacks an anchoring mechanism to prevent the distal end from migrating in the epidural space.

Figure 2:
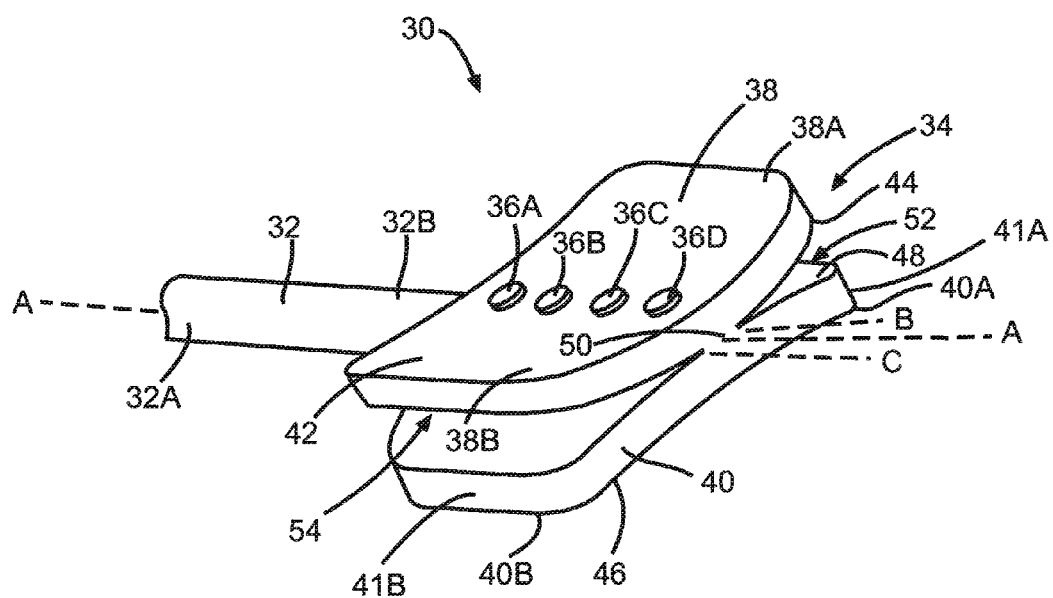
FIG. 2 is a perspective drawing of the present invention of a neurological stimulator paddle lead 30.

FIG. 2 illustrates an electrode 30 according to the present invention. Electrode 30 is comprised of a lead body 32 and a paddle body assembly 34. As FIG. 2 shows, the paddle body assembly 34 is attached to the distal region 32B of the lead body along a longitudinal axis A-A. Lead body 32 has an elongate body that extends from a proximal region 32A to the distal region 32B. Electrodes 36A, 36B, 36C and 36D are embedded in the surface of the first curved paddle body 38. The electrodes 36A-36D are shown aligned along the longitudinal axis A-A. Alternatively, the electrodes 36 could be embedded anywhere within the surface of the first curved paddle body 38. Furthermore, the embedded electrodes 36 could also have a multitude of shapes, not limited to, rectangular, square, circular, triangular, or combinations thereof. One could also design an array of electrode bands whereby the bands comprise a series of lines that are arranged in a parallel, perpendicular, circular or random pattern on the surface of the first paddle 38.

In a preferred but not limiting embodiment, the array of electrodes 36A-36D lies within the space between parallel lines B-B and C-C. The space between parallel lines B-B and C-C define an area where paddles 38 and 40 are connected to each other. This allows for the lead body 32 to connect with the series of electrodes in the center of the paddle assembly 34.

An alternate embodiment of the invention comprises an array or multitude of electrodes which lie outside parallel planes B-B and C-C within paddle 38. In a further alternate embodiment, one could design the invention with a plurality of electrodes that lie parallel to the longitudinal axis A-A such as in a column or multiple columns. Likewise, one could design the invention with a plurality of electrodes that lie perpendicular to the longitudinal axis A-A such as in a row or multiple rows. One could also design the invention with a combination of electrodes that are both parallel and perpendicular (39A-39D) to the longitudinal axis A-A.

Conductors connect the respective electrodes 36A-36D to the proximal region of the lead body 32A. Each conductor separately connects to a metal band (not shown) within the proximal region 32A of the lead and an individual electrode 36 within the distal region of the lead. The conductors reside within and traverse the length of the lead body, from the proximal region 32A to the distal region 32B thereof. The conductors are preferably wires that are composed of a silver cored material. Alternate materials such as stainless steel, platinum, platinum alloy, MP35N, titanium, silver, gold, palladium or nickel alloy in an insulated or uninsulated form can also be used. The conductor wire should be of about the length of the electrical stimulator lead 30 and of a diameter that fits freely with multiple conductor wires inside the hollow lead body 32. A preferred conductor wire diameter is about 0.1 mm and can range from about 0.025 mm to about 0.25 mm. The conductors are preferably round; however, they can also be flat or in the form of a cable.

The proximal end of the lead body 32A is connected to the header of a medical device (not shown). It is preferred that a neurostimulator is connected to the lead body 32. It is contemplated that although the present invention is intended for use with a neurostimulator to stimulate neurological tissue, one could also use the invention to stimulate cardiac tissue as well. Therefore, the present invention could be connected and used in conjunction with other implantable medical devices such as pacemakers and defibrillators.

Paddle assembly 34 is a fusion of two paddles 38 and 40. Each paddle has a concave front side 42, 46 and a convex backside 44, 48. As FIG. 2 shows, the two paddles are positioned back to back with the concave front sides 42, 46 opposing each other. The convex backsides of the two paddles 44, 48 are joined together along the longitudinal axis A-A. The connection region 50 is defined between longitudinal lines B-B and C-C which are parallel to longitudinal axis A-A. It is preferred that the length between longitudinal lines B-B and C-C is about 0.25 mm to about 2.50 mm and that the resultant concave curvature of paddles 38, 40 is between 5 to 30 degrees. The overall width of paddle assembly 34 as measured from the right side paddle end portions 38A, 40A to the left side paddle end portions 38B, 40B is about 1.0 mm to 15 mm. The overall length of paddle assembly 34 as measured from the most proximal point to the most distal point of the paddle assembly 34 along longitudinal axis A-A is about 1.0 mm to about 15.0 mm.

To control the curvature and flexibility of the paddles 38, 40, a person skilled in the art could adjust the distance between parallel lines B-B and C-C that defines the connection region 50. For example, increasing the distance between parallel lines B-B and C-C decreases the degree of curvature and flexibility of the convex paddles 38, 40. In contrast, decreasing the distance between parallel lines B-B and C-C increases the degree of curvature and flexibility of the paddles 38, 40 and the resultant paddle assembly 34.

In a preferred embodiment the concave front side surfaces 42, 46 of respective paddles 38 and 40 have a continuous curvature. The trough of the concave surface 42, 46 is parallel to axis A-A and extends from one end of the paddle to the other. However, both paddles 38, 40 could be designed with a planar region at the trough of the concave surfaces 42, 46. Such a planar portion, particularly with regards to paddle 38, would provide a planar surface to embed electrodes 36.

In the context of the present invention, the term "concave" is meant to describe a curved surface on which neighboring lines normal to the curved surface converge and on which lies the chord joining two neighboring points of the curved surface. The depth of curvature of the concave surface 46 is from about 1 percent to about 25 percent of the distance between a line tangent to where the concave surface 46 meets the end walls 41A and 41B.

Electrode 36 is shown embedded in the concave front surface of paddle 38. A portion of the electrode 36 is shown protruding from the concave front surface of the paddle 38. This protrusion allows for improved contact with the neurological tissue. Although not preferred, one skilled in the art could design the electrode 36 to not protrude from the surface of the paddle 38 and, therefore, be flush with the concave surface.

Both paddles 38 and 40 are composed of a biocompatible polymeric material, preferably silicone rubber. This material gives paddles 38, 40 a solid yet flexible structural form. Paddles 38, 40 are designed to be flexible and bend under compression without tearing or creating damage to the paddle assembly 34. Specifically end portions 38A, 38B, 40A and 40B of the respective paddles 38 and 40 are design to bend and flex independent of each other. Other biocompatible polymeric materials such as polytetrafluoroethylene (PTFE), polyurethane, and polyimide could also be used.

The flexing action of paddle end portions 40A, 40B which are curved in a concave form, create a spring like action that pushes against the bone of the spinal column and fixates the lead in place once implanted. The fusion of the two curved paddles 38, 40 create interstitial spaces 52 and 54 between the end portions of the paddles 38, 40. As the paddle end portions 38A, 383, 40A and 40B are compressed, the interstitial spaces 52 and 54 decrease. Once the compression is relieved, the interstitial spaces 52, 54 increase.

The spring like action of the flexible end portions of the paddle 40, compress paddle 38 into the dura mater 60. By compressing paddle 38 into the dura mater, the flexible curved end portions of paddle 38 conform to the curved shape of the dura mater 60, thereby stabilizing and fixating the paddle assembly 34 into place.

Compression of the first paddle 38 into the neurological tissue also improves the stimulation efficiency by focusing the electrical energy directly to the area of intended stimulation. The conforming front surface 42 of the first paddle 38 directs the electrical energy to a focused point or area of stimulation. The electrical energy is no longer being emitted indiscriminately in an array of directions.

Figure 3:
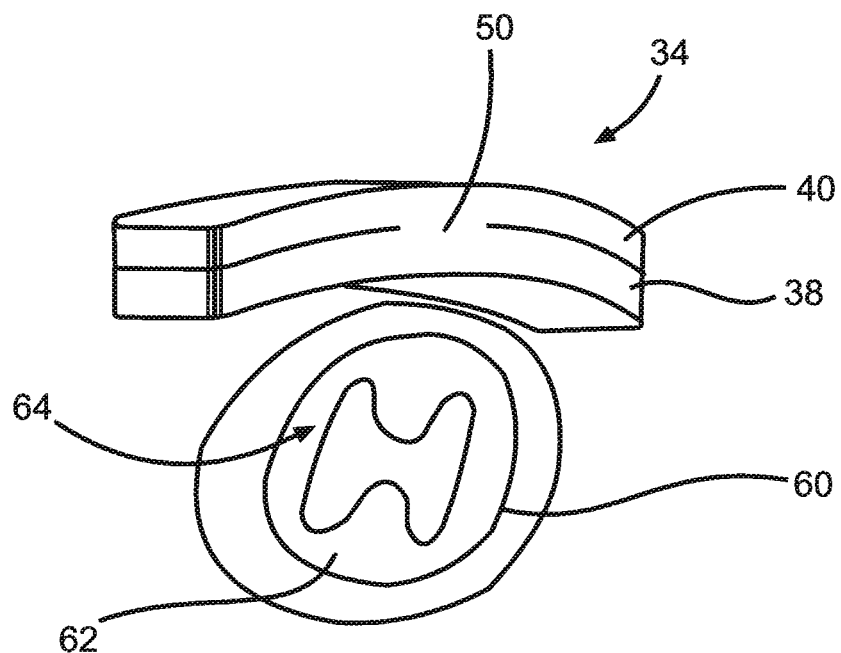
FIG. 3 is a cross-sectional view of the paddle assembly 34 implantation site taken along a horizontal axis of a patient before implantation.
Figure 4:
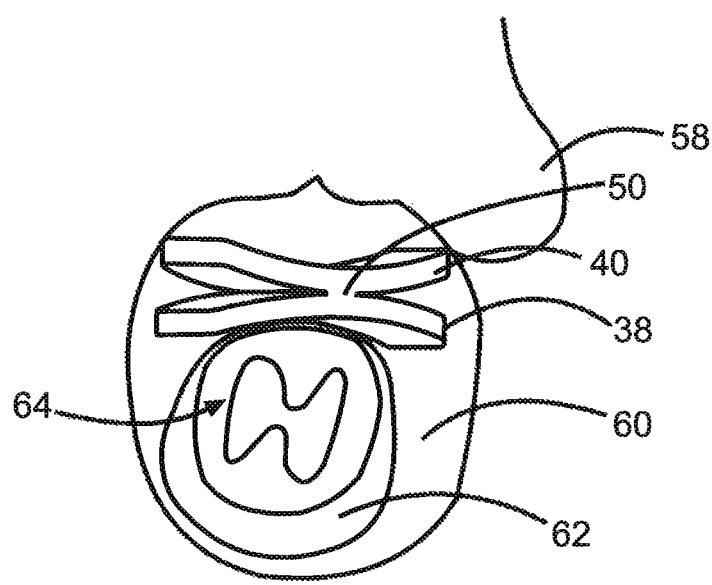
FIG. 4 is a cross-sectional view of the paddle assembly 34 implantation site taken along a horizontal axis of a patient after implantation.

As shown in FIGS. 3 and 4, compression of paddle 38 into the dura mater 60 restricts the flow of cerebral spinal fluid (CSF) 62 along the side of the implanted paddle assembly 34. CSF is a biological fluid that flows between the spinal cord 64 and the dura mater 60. The restriction of CSF 62 improves the efficiency of the electrical energy in reaching the targeted neurological tissue of the spinal cord. 64 from the electrodes 36A-36D. First, reduction of the distance between the electrodes 36 of the paddle assembly 34 and the spinal cord 64 reduces the amount of CSF through which electrical energy must pass. Secondly, CSF 62 has been known to diffuse electrical signals. Reducing the amount of CSF 62 reduces undesirable signal diffusion and improves electrical signal efficiency.

FIG. 2 depicts the preferred embodiment in which there are four individual electrodes 36A-36D. One of the conductors is connected to a specific electrode pad. Although it is preferred to have four electrodes 36A-36D, one skilled in the art could design such a lead with fewer or more than four electrodes as desired.

The paddle assembly 34 is implanted in the epidural space between the spinal column 58 and spinal cord 64, specifically the space between the spinal column 58 and the dura mater 60 of the spinal cord 64. Paddle 38, with embedded electrodes 36A-36D, is positioned towards the dura mater 60 so the electrodes are in contact with the dura mater 60.

The lead is implanted by first accessing the targeted area along the spinal column. The curved paddles 38, 40 of the paddle assembly 34 are compressed together for insertion into the epidural space. Once inserted, paddles 38, 40 are released, expanding the area of the interstitial space 52, 54 and compressing the paddle assembly 34 into place.

FIG. 4 illustrates the implanted paddle assembly 34 after implantation between the spinal column 58 and dura mater 60. As the figure illustrates, the concaved paddle 40 is compressed against the bone of the spinal column 58 and the concaved paddle 38 is compressed against the dura mater 60. Paddle end portions 40A and 40B are pushing against the spinal column 58. The paddle lead is now confined into place and cannot move. As the figure illustrates, the space between the dura mater 60 and spinal cord 64 is reduced due to the compression of the paddle assembly 34 towards the spinal cord 64. Reduction in the space between the electrode side of the paddle assembly and the dura 60 not only confines the paddle assembly 34 into place, but also restricts the flow of CSF and reduces the gap between the dura mater 60 and the targeted neurological tissue 64. Therefore, the electrical efficiency of the medical device system is improved. A shorter transmission distance is now required and there is less impedance created by CSF 62 which diffuses the electrical signal being emitted from the electrode 36.

It is appreciated that various modifications to the inventive concepts described herein may be apparent to those of ordinary skill in the art without departing from the scope of the present invention as defined by the appended claims.

What is claimed is:
1. An electrical lead comprising:
 a) an elongate lead body comprising a plurality electrical conductors, each having a length extending from a proximal region to a distal region of the lead;
 b) a first curved paddle body with a concave front-side and a convex backside, both sides extending to and meeting spaced apart right and left first edges;
 c) a second curved paddle body with a concave front side and a convex backside, both sides extending to and meeting spaced apart right and left second edges,
  i) wherein the convex backside of the first paddle body directly contacts the convex backside of the second paddle body in a back-to-back relationship to thereby form a paddle body assembly, and
ii) wherein an imaginary plane extends through the lead body along the length thereof and through where the first paddle body contacts the second paddle body in the back-to-back relationship such that the right and left edges of the respective first and second paddle bodies reside on opposite sides of the imaginary plane;
d) a plurality of electrodes disposed on the concave front-side of the first paddle body;
e) wherein the distal region of the lead is connected to the paddle body assembly;
f) wherein the plurality of conductors extend from the proximal region of the lead and connect with the electrodes; and
g) wherein the proximal region of the lead is connectable to a header of an implantable medical device.

2. The lead of claim 1 wherein the convex backside of the first paddle body directly contacts the convex backside of the second paddle body along a longitudinal axis of the paddle body assembly.

3. The lead of claim 1 wherein the plurality of electrodes lie parallel to a longitudinal axis of the paddle body assembly.

4. The lead of claim 1 wherein the plurality of electrodes lie perpendicular to a longitudinal axis of the paddle body assembly.

5. The lead of claim 1 wherein the first and second paddle bodies are composed of a biocompatible polymeric material.

6. The lead of claim 5 wherein the biocompatible polymeric material is silicone rubber.

7. The lead of claim 1 wherein the surface of the concave front-side of the first paddle body has a continuous curvature.

8. The lead of claim 1 wherein the surface of the concave front-side of the second paddle body has a continuous curvature.

9. The lead of claim 1 wherein the surface of the concave front-side of the first paddle body has a planar portion.

10. The lead of claim 1 wherein the surface of the concave front-side of the second paddle body has a planar portion.

11. An electrical stimulation lead comprising:
a) an elongate lead body comprising a plurality of electrical conductors, each having a length extending from a proximal region to a distal region of the lead;
b) a first curved paddle body with a concave front-side and a convex backside, both sides extending to and meeting spaced apart right and left first edges;
c) a second curved paddle body with a concave front side and a convex backside, both sides extending to and meeting spaced apart right and left second edges,
i) wherein the convex backside of the first paddle body directly contacts the convex backside of the second paddle body in a back-to-back relationship to form a paddle body assembly, and
ii) wherein an imaginary plane extends through the lead body along the length thereof and through where the first paddle body contacts the second paddle body in the back-to-back relationship such that the right and left edges of the respective first and second paddle bodies reside on opposite sides of the imaginary plane;
d) a plurality of electrodes disposed on the concave front-side of the first paddle body, wherein at least one of the electrodes protrudes out beyond a front surface formed by the concave front-side thereof;
e) wherein the distal region of the lead is connected to the paddle body assembly;
f) wherein the plurality of conductors extend from the proximal region of the lead and connect with the electrodes; and
g) wherein the proximal region of the lead is connected to a header of an implantable medical device.

12. The lead of claim 11 wherein the convex backside of the first paddle body directly contacts the convex backside of the second paddle body along a longitudinal axis of the paddle body assembly.

13. The lead of claim 11 wherein the first and second paddle bodies are composed of a biocompatible polymeric material.

14. The lead of claim 13 wherein the biocompatible polymeric material is silicone rubber.

15. The lead of claim 11 wherein the implantable medical device is selected from the group consisting of a neurostimulator, a pacemaker and a defibrillator.

16. A method for electrically stimulating a body tissue, comprising the steps of:
a) providing an elongate lead body comprising:
i) a plurality of electrical conductors, each having a length extending from a proximal region to a distal region of the lead;
ii) a first curved paddle body with a concave front-side and a convex backside;
iii) a second curved paddle body with a concave front side and a convex backside, wherein the convex backside of the first paddle body directly contacts the convex backside of the second paddle body in a back-to-back relationship to form a paddle body assembly;
b) providing a plurality of electrodes disposed on the concave front-side of the first paddle body, wherein the distal region of the lead is connected to the paddle body assembly;
c) compressing ends of the first and second paddle bodies spaced from where the first paddle body contacts the second paddle body to thereby provide a compressed body assembly;
d) inserting the compressed paddle body assembly between the spinal column and dura mater of a human;
e) releasing the ends of the first and second paddle bodies; and
f) connecting the lead to an implantable medical device.

17. The method of claim 16 including providing the convex backside of the first paddle body directly contacting the convex backside of the second paddle body along a longitudinal axis.

18. The method of claim 16 including providing the first and second paddle bodies being composed of a biocompatible polymeric material.

19. The method of claim 18 wherein the biocompatible polymeric material is silicone rubber.

20. The method of claim 16 including selecting the implantable medical device from the group consisting of a neurostimulator, a pacemaker and a defibrillator.

* * * * *